(12) United States Patent
Grande et al.

(10) Patent No.: US 6,214,369 B1
(45) Date of Patent: Apr. 10, 2001

(54) MESENCHYMAL STEM CELLS FOR CARTILAGE REPAIR

(75) Inventors: Daniel A. Grande, Sea Cliff, NY (US); Paul A. Lucas, Macon, GA (US)

(73) Assignee: MorphoGen Pharmaceuticals, Inc., Downey, CA (US)

( * ) Notice: Subject to any disclaimer, the term of this patent is extended or adjusted under 35 U.S.C. 154(b) by 0 days.

(21) Appl. No.: 09/306,487

(22) Filed: May 6, 1999

Related U.S. Application Data

(63) Continuation of application No. 08/403,640, filed on Mar. 14, 1995, now Pat. No. 5,906,934.

(51) Int. Cl.⁷ ........................................................ A61F 2/00
(52) U.S. Cl. .............................................................. 424/423
(58) Field of Search .............................................. 424/423

(56) References Cited

U.S. PATENT DOCUMENTS

| | | | |
|---|---|---|---|
| 5,041,138 | * | 8/1991 | Vacanti et al. .......................... 623/16 |
| 5,486,359 | | 1/1996 | Caplan et al. ....................... 424/93.7 |
| 5,902,741 | | 5/1999 | Purchio et al. .................. 435/240.23 |

* cited by examiner

*Primary Examiner*—Theodore J. Criares
(74) *Attorney, Agent, or Firm*—Klauber & Jackson

(57) ABSTRACT

It has been discovered that mesenchymal stem cells (MSCs) in a polymeric carrier implanted into a cartilage and/or bone defect will differentiate to form cartilage and/or bone, as appropriate. Suitable polymeric carriers include porous meshes or sponges formed of synthetic or natural polymers, as well as polymer solutions. A presently preferred material is a polyglycolic acid mesh.

17 Claims, No Drawings

MESENCHYMAL STEM CELLS FOR CARTILAGE REPAIR

This application is a continuation of application Ser. No. 08/403,640 filed Mar. 14, 1995, now U.S. Pat. No. 5,906,934.

BACKGROUND OF THE INVENTION

The present invention is generally in the area of regeneration and repair of cartilage, and more particularly relates to implantation of mesenchymal stem cells on matrices to form cartilage.

Arthritis, both rheumatoid and osteoarthritis, constitutes a major medical problem. In particular, degeneration of articular cartilage in osteoarthritis is a serious medical problem. Drugs are given to control the pain and to keep the swelling down, but the cartilage continues to be destroyed. Eventually, the joint must be replaced. As reviewed by Mankin, *N. E. J. Med.* 331(14), 940–941 (October 1994), it is still unknown why cartilage does not heal and no solutions to this problem are known.

Whether articular cartilage is damaged from trauma or congenital anomalies, its successful clinical regeneration is poor at best, as reviewed by Howell, et al. *Osteoarthritis: Diagnosis and Management,* 2nd ed., (Philadelphia, W. B. Saunders, 1990) and Kelley, et al. *Textbook of Rheumatology,* 3rd ed., (Philadelphia, W. B. Saunders, 1989) 1480. The inability of adult articular cartilage for self repair has been well recognized and has stimulated major interest. There are two major mechanisms of articular cartilage repair: intrinsic and extrinsic, discussed by Edwards *Proc. Ins. Mech. Eng.* 181, 16 (1967), and Sokoloff *J. Rheumatol.* 1, 1 (1974).

Superficial or partial-thickness injuries that do not penetrate the subchondral bone rely on the intrinsic mechanism for repair. Soon after superficial injury, chondrocytes adjacent to the injured surfaces show a brief burst of mitotic activity associated with an increase in glycosaminoglycan and collagen synthesis. Despite these attempts at repair, there is no appreciable increase in the bulk of cartilage matrix and the repair process is rarely effective in healing the defects.

Osteochondral, or full-thickness, cartilage defects extend into the subchondral bone. Such defects arise after the detachment of osteochondritic dissecting flaps, fractured osteochondral fragments, or from chronic wear of degenerative articular cartilage. Osteochondral defects depend on the extrinsic mechanism for repair. Extrinsic healing relies on mesenchymal elements from subchondral bone to participate in the formation of new connective tissue. This fibrous tissue may or may not undergo metaplastic changes to form fibrocartilage. Even if fibrocartilage is formed, it does not display the same biochemical composition or mechanical properties of normal articular cartilage or subchondral bone and degenerates with use, Furukawa, et al., *J. Bone Joint Surg.* 62A, 79 (1980); Coletti, et al., *J. Bone Joint Surg.* 54A, 147 (1972); Buckwalter, et al., "Articular cartilage: composition, structure, response to injury and methods of facilitating repair", in *Articular Cartilage and Knee Joint Function: Basic Science and Arthroscopy,* Ewing J E, Ed., (New York, Raven Press, 1990), 19. The ensuing osteoarthritis may result in permanent disability and discomfort to the patient.

As described in U.S. Pat. No. 5,041,138 to Vacanti, et al., and U.S. Pat. No. 4,846,835 to Grande, cartilage has been grown by seeding synthetic polymeric matrices with dissociated cells, which are then implanted to form new cartilage. Cartilage has also been grown from an injected or implanted ionically crosslinked hydrogel-chondrocyte suspension, as described by Atala, et al., *J. Urology* vol. 150, no. 2, part 2, 745–747 (August 1993). Injection of dissociated chondrocytes directly into a defect has also recently been described as a means for forming new cartilage, as reported by Brittberg, et al., *N. E. J. Med.* 331,889–895 (October 1994). Cartilage was harvested from minor load-bearing regions on the upper medial femoral condyle of the damaged knee, cultured, and implanted two to three weeks after harvesting.

Freed and Grande, *J. Biomed. Mater. Res.* 28, 891 (1994) cultured mature chondrocytes from New Zealand white rabbits in vitro onto polyglycolic acid (PGA) scaffolds for 2½ weeks. A full thickness articular cartilage defect was then created in the femoropatellar groove bilaterally in syngeneic New Zealand white rabbits. Mature chondrocytes on the PGA-matrix (PGA-cells) were imbedded into one knee joint while PGA discs alone were imbedded into the contralateral knee and the animals euthanized at one and six months post-implantation. The repair tissue was well bonded to the host tissue and the surfaces of these defects were congruent with the host cartilage. The PGA alone showed a mixture of fibrocartilage and hyaline cartilage oriented randomly. The PGA-cells implant showed normal articular cartilage histology, but did not have normal subchondral bone.

A disadvantage of these systems is that the chondrocytes must be obtained from the patient, typically by a biopsy, cultured, and then implanted on the matrix. This is relatively easy in laboratory animals, but presents greater logistical problems in humans where a defect is created by the biopsy required to provide cells for repair of another defect. Moreover, if the defect includes a part of the underlying bone, this is not corrected using chondrocytes, which are already differentiated and will not form new bone. The bone is required to support the new cartilage.

Stem cells are defined as cells which are not terminally differentiated, which can divide without limit, and divides to yield cells that are either stem cells or which irreversibly differentiate to yield a new type of cell. Those stem cells which give rise to a single type of cell are call unipotent cells; those which give rise to many cell types are called pluripotent cells. Chondro/osteoprogenitor cells, which are bipotent with the ability to differentiate into cartilage or bone, were isolated from bone marrow (for example, as described by Owen, *J. Cell Sci. Suppl.* 10, 63–76 (1988) and in U.S. Pat. No. 5,226,914 to Caplan, et al.). These cells led Owen to postulate the existence of pluripotent mesenchymal stem cells, which were subsequently isolated from muscle (Pate, et al., *Proc. 49th Ann. Sess. Forum Fundamental Surg. Problems* 587–589 (Oct. 10–15, 1993)), heart (Dalton, et al., *J. Cell Biol.* 119, R202 (March 1993)), and granulation tissue (Lucas, et al., *J. Cell Biochem.* 122, R212 (March 1993)). Pluripotency is demonstrated using a non-specific inducer, dexamethasone (DMSO), which elicits differentiation of the stem cells into chondrocytes (cartilage), osteoblasts (bone), myotubes (muscle), adipocytes (fat), and connective tissue cells.

Unfortunately, although it is highly desirable to have stem cells which are easily obtained by a muscle biopsy, cultured to yield large numbers, and can be used as a source of chondrocytes or osteoblasts or myocytes, there is no known specific inducer of the mesenchymal stem cells that yields only cartilage. In vitro studies in which differentiation is achieved yields a mixture of cell types. Studies described in U.S. Pat. Nos. 5,226,914 and 5,197,985 to Caplan, et al., in which the cells were absorbed into porous ceramic blocks and implanted yielded primarily bone. Studies using bone morphogenic protein-2 (rhBMP-2) in vivo always yield an endochondral bone cascade. That is, cartilage is formed first, but this cartilage hypertrophies, is invaded by vasculature and osteoblasts, and is eventually replaced by bone complete with marrow (Wozney, *Progress in Growth Factor Research* 1, 267–280 (1989)). Studies testing rhBMP-2 on the mesenchymal stem cells in vitro produced mixtures of differentiated cells, although cartilage predominated (Dalton, et al., *J. Cell Biol.* 278, PZ202 (February 1994)). Incubation of mesenchymal cell cultures with insulin led to a mixed myogenic and adipogenic response, while incubation with insulin-like growth factors I or II led to a primarily myogenic response (Young, et al., *J. Cell Biochem.* 136, CD307 (April 1992)). U.S. Pat. Nos. 4,774,322 and 4,434,094 to Seyedin, et al., report the isolation of a factor that induces an osteogenic response in vivo or cartilage formation in vitro when mixed with muscle cells.

It is therefore an object of the present invention to provide a method and compositions for formation of cartilage.

It is a further object of the present invention to provide a method and compositions to induce differentiation of mesenchymal stem cells into cartilage.

SUMMARY OF THE INVENTION

It has been discovered that mesenchymal stem cells (MSCs) in a polymeric carrier implanted into a cartilage and/or bone defect will differentiate to form cartilage and/or bone, as appropriate.

Suitable polymeric carriers include porous meshes or sponges formed of synthetic or natural polymers, as well as polymer solutions. A presently preferred material is a polyglycolic acid mesh.

As demonstrated by the examples, MSCs were isolated from adult rabbit muscle and cultured in vitro in porous polyglycolic acid polymer matrices. The matrices were implanted into three mm diameter full thickness defects in rabbit knees with empty polymer matrices serving as the contralateral controls. The implants were harvested six and 12 weeks post-op. At six weeks, the controls contained fibrocartilage while the experimentals contained undifferentiated cells. By 12 weeks post-op, the controls contained limited fibrocartilage and extensive connective tissue, but no subchondral bone. In contrast, the implants containing MSCs had a surface layer of cartilage approximately the same thickness as normal articular cartilage and normal-appearing subchondral bone. There was good integration of the implant with the surrounding tissue. Implantation of MSCs into cartilage defects effected repair of both the articular cartilage and subchondral bone.

DETAILED DESCRIPTION OF THE INVENTION

I. Isolation and Preparation of MSCs.

Mesenchymal stem cells (MSCs) are isolated from connective tissue, including muscle and dermis. They have advantages based on their unlimited growth potential and their ability to differentiate into several phenotypes of the mesodermal lineage, including cartilage and bone.

MSCs are preferably isolated from muscle using a standard punch or dermal biopsy. However, MSCs can be obtained from bone marrow or other mesenchymal tissues.

A detailed procedure for isolation of MSCs from embryonic chick muscle is described by Young, et al., *J. Tiss. Cult. Meth.* 14, 85–92 (1992), the teachings of which are incorporated by reference herein. The same basic procedure is used for isolation of mammalian MSCs from muscle. Muscle is removed, rinsed, minced and the cells isolated by digestion with collagenase/dispase and cultured in gelatin-coated dishes in EMEM or DMEM media with pre-selected horse serum (serum is pre-screened for support of MSCs but not fibroblasts) until confluent. The cells are trypsinized and slowly frozen in freezing chambers 7.5% DMSO at −80° C. The cells are then thawed and cultured in the same media without DMSO. Freezing is used to kill any fibroblasts present in the cell culture. Filtration through 20 micron Nitex is used to remove myotubes. Reagents can be obtained from Sigma Chemical Co., St. Louis, Mo. or GIBCO, Grand Island, N.Y.

II. Polymeric Matrices.

There are basically two types of matrices that can be used to support the MSCs as they differentiate into cartilage or bone. One form of matrix is a polymeric mesh or sponge; the other is a polymeric hydrogel. In the preferred embodiment, the matrix is biodegradable over a time period of less than a year, more preferably less than six months, most preferably over two to ten weeks. In the case of joint surface application, the degradation period is typically about twelve to twenty-four weeks. In the case where weight bearing or high shear stress is not an issue, the degradation period is typically about five to ten weeks. The term bioerodible or biodegradable, as used herein, means a polymer that dissolves or degrades within a period that is acceptable in the desired application, less than about six months and most preferably less than about twelve weeks, once exposed to a physiological solution of pH 6–8 having a temperature of between about 25° C. and 38° C. The polymer composition, as well as method of manufacture, can be used to determine the rate of degradation. For example, mixing increasing amounts of polylactic acid with polyglycolic acid decreases the degradation time.

A. Fibrous Matrices.

Polymeric Materials.

Fibrous matrices can be manufactured or constructed using commercially available materials. The matrices are typically formed of a natural or a synthetic polymer. Biodegradable polymers are preferred, so that the newly formed cartilage can maintain itself and function normally under the load-bearing present at synovial joints. Polymers that degrade within one to twenty-four weeks are preferable. Synthetic polymers are preferred because their degradation rate can be more accurately determined and they have more lot to lot consistency and less immunogenicity than natural polymers. Natural polymers that can be used include proteins such as collagen, albumin, and fibrin; and polysaccharides such as alginate and polymers of hyaluronic acid. Synthetic polymers include both biodegradable and non-biodegradable polymers. Examples of biodegradable polymers include polymers of hydroxy acids such as polylactic acid (PLA), polyglycolic acid (PGA), and polylactic acid-glycolic acid (PLGA), polyorthoesters, polyanhydrides, polyphosphazenes, and combinations thereof. Non-biodegradable polymers include polyacrylates, polymethacrylates, ethylene vinyl acetate, and polyvinyl alcohols. These should be avoided since their presence in the cartilage will inevitably lead to mechanical damage and breakdown of the cartilage.

Matrix Construction.

In the preferred embodiment, the polymers form fibers which are intertwined, woven, or meshed to form a matrix having an interstitial spacing of between 100 and 300 microns. Meshes of polyglycolic acid that can be used can be obtained from surgical supply companies such as Ethicon, N.J. Sponges can also be used. As used herein, the term "fibrous" refers to either a intertwined, woven or meshed matrix or a sponge matrix.

The matrix is preferably shaped to fill the defect. In most cases this can be achieved by trimming the polymer fibers with scissors or a knife; alternatively, the matrix can be cast from a polymer solution formed by heating or dissolution in a volatile solvent.

Application of the Cells

The MSCs are seeded onto the matrix by application of a cell suspension to the matrix. This can be accomplished by soaking the matrix in a cell culture container, or injection or other direct application of the cells to the matrix. Media should be washed from the cells and matrix prior to implantation.

The matrix seeded with cells is implanted at the site of the defect using standard surgical techniques. The matrix can be seeded and cultured in vitro prior to implantation, seeded and immediately implanted, or implanted and then seeded with cells. In the preferred embodiment, cells are seeded onto and into the matrix and cultured in vitro for between approximately sixteen hours and two weeks. It is only critical that the cells be attached to the matrix. Two weeks is a preferred time for culture of the cells, although it can be longer. Cell density at the time of seeding or implantation should be approximately 25,000 cells/mm$^3$.

B. Hydrogel Matrices.

Hydrogel matrices are described, for example, in PCT US94/04710 by Massachusetts Institute of Technology and Childrens Medical Center Corporation, the teachings of which are incorporated herein.

Polymers that can form ionic or covalently crosslinked hydrogels which are malleable are used to encapsulate cells. For example, a hydrogel is produced by cross-linking the anionic salt of polymer such as alginic acid, a carbohydrate polymer isolated from seaweed, with calcium cations, whose strength increases with either increasing concentrations of calcium ions or alginate. The alginate solution is mixed with the cells to be implanted to form an alginate suspension. Then the suspension is injected directly into a patient prior to hardening of the suspension. The suspension then hardens over a short period of time due to the presence in vivo of physiological concentrations of calcium ions.

The polymeric material which is mixed with cells for implantation into the body should form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Polymers can be synthesized that degrade by hydrolysis by incorporating monomers having imidazole, amino acid ester, or glycerol side groups. For example, a polyanionic poly [bis(carboxylatophenoxy)]phosphazene (PCPP) can be synthesized, which is cross-linked with dissolved multivalent cations in aqueous media at room temperature or below to form hydrogel matrices.

The water soluble polymer with charged side groups is ionically crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, zinc, and tin, although di-, tri- or tetra-functional organic cations such as alkylammonium salts, e.g., $R_3N^+$ –\/\/\/–$^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

Cell Suspensions

Preferably the polymer is dissolved in an aqueous solution, preferably a 0.1 M potassium phosphate solution, at physiological pH, to a concentration forming a polymeric hydrogel, for example, for alginate, of between 0.5 to 2% by weight, preferably 1%, alginate. The isolated cells are suspended in the polymer solution to a concentration of between 1 and 10 million cells/ml, most preferably between 10 and 20 million cells/ml.

Methods of Implantation.

In the preferred embodiment, the cells are mixed with the hydrogel solution and injected directly into a site where it is desired to implant the cells, prior to hardening of the hydrogel. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. One could also apply an external mold to shape the injected solution. Additionally, by controlling the rate of polymerization, it is possible to mold the cell-hydrogel injected implant like one would mold clay.

Alternatively, the mixture can be injected into a mold, the hydrogel allowed to harden, then the material implanted.

The suspension can be injected via a syringe and needle directly into a specific area wherever a bulking agent is desired, especially soft tissue defects. The suspension can also be injected as a bulking agent for hard tissue defects, such as bone or cartilage defects, either congenital or acquired disease states, or secondary to trauma, burns, or the like. An example of this would be an injection into the area surrounding the skull where a bony deformity exists secondary to trauma. The injection in these instances can be made directly into the needed area with the use of a needle and syringe under local or general anesthesia.

The suspension can be injected percutaneously by direct palpation. Alternatively, the suspension can be injected through a catheter or needle with fluoroscopic, sonographic, computer tomography, magnetic resonance imaging or other type of radiologic guidance.

III. Conditions to be Treated.

The mesenchymal stem cells in and/or on a polymeric carrier can be used to create or supplement connective tissue as required. In some cases, this will be to repair existing defects, for example, worn or torn cartilage in joint linings. In other cases, it may be to create new tissue that performs a distinct function, such as to block tubes such as the fallopian tubes or vas derens, or to decrease reflux due to urine leakage arising from incorrect placement of the ureter into the bladder. The selection of the form of the matrix, as well as the composition, will in many cases be determined by the function to be achieved, as discussed above.

Examples of situations in which new connective tissue is particularly desirable, in addition to cartilage replacement or supplementation, include reconstruction of the spine, pubic symphysis or temporomandibular joint (TMJ).

In some cases, it may be desirable to induce a mixed cell tissue, for example, in breast reconstruction. Breast tissue is naturally composed of fat, cartilage and other connective tissue, muscle and other tissues. New breast tissue can be formed by implanting mesenchymal cells in a polymeric carrier in a fascial plane formed of muscle cells, fat, fibroblasts, and cartilage.

The present invention will be further understood by reference to the following non-limiting examples.

EXAMPLE 1

Implantation of MSCs on PGA Scaffolds and Implantation Into Full Thickness Articular Cartilage Defects in Rabbits This experiment was conducted to determine the regenerative capabilities of MSCs cultured on the PGA scaffolds and placed into syngeneic rabbit full thickness articular cartilage defects.

Materials and Methods:

New Zealand white rabbits were purchased from Hazelton (Denver, Pa.). Polyglycolic acid (PGA) discs, non-woven fiber mats, 1 cm diameter×0.2 cm thick, composed of 12–14 $\mu$m diameter fibers at a density of 55–65 mg/cm$^3$ and sterilized with ethylene oxide were obtained from Albany International, Mansfield, Mass.

Rabbit MSCs were isolated as described by Pate et al *Surgical Forum* 44, 587 (1993). Briefly, adult rabbit leg skeletal muscle was harvested under sterile conditions and placed in minimal essential medium with Earle's salts (EMEM) supplemented with 3×antibiotic-antimycotic solution for at least 10 minutes. The muscle was then finely minced with scissors. The media and tissue were centrifuged at 150×g for 10 minutes, the supernatant was discarded, and the tissue was transferred to a sterile bottle containing a magnetic stir bar. The tissue was then digested with a collagenase/dispase solution consisting of 250 U/ml Worthington CLSI collagenase, Freehold, N.J., and 33 U/ml Collaborative Research dispase, Cambridge, Mass., in the ratio of 1:4:15 (v/v/v) of tissue:collagenase/dispase:EMEM. Digestion required approximately 45 minutes. The digested tissue was then centrifuged at 300×g for 20 minutes, the supernatant discarded, and the cell pellet resuspended in EMEM+10% horse serum (Sigma, lot #90H-701 Sigma, St. Louis, Mo.) with penicillin-streptomycin antibiotic (Gibco, Long Island, N.Y.). The suspension was then filtered a through 20-$\mu$m NITEX filter and an aliquot of the cells counted on a hemocytometer. The cells were plated at 105 per 100 mm gelatin-coated culture dish (Falcon, Norcross, Ga.). These cultures were termed "primary culture".

The cells were maintained for 7–10 days with media changes every 3 days until the cell layer was confluent. The cells were then detached from the dish with 0.025% trypsin in a solution of 3:1 Dulbecco's phosphate-buffered saline (DPBS) without $Ca^{2+}$, $Mg^{2+}$, and DPBS-EDTA. The trypsin was neutralized with horse serum and the suspension was centrifuged at 150×g for 20 minutes. The supernatant was discarded, the cell pellet resuspended in EMEM+10% horse serum and the cells filtered through a 20 $\mu$m nitex filter. The cells were counted on a hemocytometer, the concentration adjusted to $2\times10^6$ cells/ml, and 0.5 ml of cell suspension placed in a cryovial to which was added 0.5 ml of 15% dimethylsulfoxide (DMSO) in media (final concentration of 7.5% DMSO). The cells were then placed in freezing chamber (Fisher) and slowly frozen to −80° C. After at least 16 hours, the cells were thawed and plated at 100,000 cells per 100 mm gelatin-coated culture dish and grown to confluence. This is termed "secondary culture" and consists of mesenchymal stem cells.

The cells were released from the dishes with trypsin treatment and cultured on polymer scaffolds in 35 mm tissue-culture treated polystyrene dishes. Each disk was initially seeded with $4\times10^6$ cells in a volume of 100 $\mu$l. Samples were incubated at 37° C. in a humidified atmosphere containing 5% $CO_2$ to permit cell adhesion to, and entrapment within, the polymer scaffold; 2.5 ml of culture medium were then carefully added after 6 hr, and 1.5 ml after 24 more hr. Medium was replaced every 2–3 days for 2½ weeks of tissue culture.

The full thickness cartilage defect was made according to the procedure described by Freed and Grande, *J. Biomed. Mater. Res.* 28, 891 (1994). New Zealand white rabbits were used according to N.I.H. guidelines for the care of laboratory animals (N.I.H. publication #85-23 Rev. 1985). The rabbits, 8 month old males weighing approximately 4.5 kg, were placed under general anesthesia with xylazine (5 mg/kg i.m.), and ketamine (35 mg/kg i.m.), then shaved and scrubbed with betadine. A medial parapatellar arthrotomy was performed bilaterally with the rabbit supine. A pointed 3 mm diameter custom drill bit (Acufex, Mansfield, Mass.) was used to create a full thickness defect (1–2 mm deep) in the femoropatellar groove (FPG). An attempt was made to extend this defect just through the subchondral plate without violating the subchondral bone. A surgical trephine (Biomedical Research Instruments, Wakerville, Md.) was used to core a 4 mm diameter×2 mm thick piece of PGA matrix, and this was press-fit into the 3 mm diameter defect in the rabbit's FPG. The incision was closed in two layers; the fascia was closed with interrupted 4.0 VICRYL® (absorbable) and the skin was closed with the same interrupted 4.0 VICRYL®.

The knee joints were not immobilized postoperatively, and the animals were allowed free cage activity. Rabbits were euthanized after 6 and 12 weeks using an overdose of pentobarbital. The protocol for euthanasia was 1 cc of Ketamine intramuscularly (i.m.), wait fifteen minutes, then 5 cc of SLEEP-AWAY® i.m. (Fort Dodge Lab, Fort Dodge, Iowa).

Four adult male rabbits had PGA-stem cell implants into their right knee while the left knee served as a control with only the PGA matrix being implanted. Two rabbits were euthanized at six weeks and other two rabbits euthanized at twelve weeks.

Joint repair was assessed histologically as follows. Knee joints were harvested, fixed in formalin, and decalcified in 5% nitric acid for 5–7 days, with daily changes of the nitric acid, and bisected in a coronal plane through the center of the defect. Samples were then processed for embedding in paraffin, sectioned (6 $\mu$m thick), and stained using hematoxylin & eosin or Safranin-0, then viewed at 25 to 200× magnification by light and phase contrast microscopy.

Results:

Mesenchymal stem cells were isolated from rabbit muscle and grown to confluence in culture. These cells have the characteristic mononuclear, stellate shape associated with MSCs isolated previously from chick and rat skeletal muscle. When the MSCs were cultured in the PGA matrix, the cells adhered to the matrix but did not differentiate. There was no apparent cartilage matrix.

The defects containing PGA polymer alone (control) at six weeks show a small amount of matrix from the dissolving PGA disc among the abundant fibrous elements. There was a definite boundary between the implant and the host cartilage with no presence of articular cartilage in the implant. There were non-specific fibrocartilage cells and abundant collagenous matrix in the control at 6 weeks. The PGA-MSC matrices at six weeks resembled the controls. There were relatively undifferentiated cells and nests of apparent cartilage. Remnants of the PGA matrix were also present.

Normal articular cartilage was present adjacent to the defect. The cells could be seen in lacunae. The proliferative zone with isogenous nests was clearly visible, as is the tidemark. At twelve weeks, the controls had a patchy mixture of fibrous and hyaline cartilage and extensive connective tissue. There was no evidence of new subchondral bone. The surface layer of cells appeared fibroblastic, lacking the round lacunae characteristic of hyaline cartilage, and were oriented perpendicular to the surface.

In contrast, the PGA-MSC matrices at 12 weeks showed a surface layer of cartilage approximately the same thickness as the host cartilage and normal appearing subchondral bone. The surface layer of cartilage contained chondrocytes within lacunae surrounded by cartilaginous matrix. Isogenous nests could be discerned. There were also islands of apparent mesenchymal stem cells. Beneath the cartilage, a tidemark was seen in places. Trabecular, cortical bone underlay the cartilage, complete with hematopoietic tissue. There was good integration of the tissue in the defect with the surrounding tissue.

Discussion:

The data shows the successful regeneration of articular cartilage defects using mesenchymal stem cells harvested from rabbit muscle. The MSCs were obtained from rabbit muscle. When cultured in media, the MSCs maintain an undifferentiated phenotype but, when treated with dexamethasone, they differentiate into a number of mesodermal phenotypes. This behavior in vitro is identical to MSCs isolated from rat and chick.

There is little difference between control and experimental defects at 6 weeks post-op. However, by 12 weeks post-op, there are dramatic differences between the two treatments. The PGA-MSC matrix at has similar histology to normal cartilage. A layer of cartilage and subchondral bone are evident and it is difficult to ascertain the edge of the experimental implant even at 200×magnification. The experimental defects had a good, but not perfect, articular surface, with occasional defects at higher magnifications. The surface is the same thickness as the surrounding cartilage. The subchondral bone, however, is indistinguishable from that seen in normal articular cartilage, and it is impossible to determine the base of the defect.

In contrast, the control defects at 12 weeks post-op are filled with apparent fibrocartilage. This is particularly evident in the area adjacent to the surface. Deeper, the defect contains chondrocytes in large lacunae. There is no evidence of subchondral bone, and the interface between defect and surrounding tissue is obvious.

It appears that the MSCs differentiate into chondrocytes and osteoblasts within the defect. It appears the MSCs differentiate in such a manner as to re-create the spatial orientation of the tissue, cartilage at the surface and bone underneath. The signals mediating this differentiation are unknown. Presumably, the cells respond to endogenous signals emanating from the surrounding cartilage and bone, although other sources such as synovial fluid and blood cannot be eliminated. There may also be mechanical signals, although the defect site in the femoropatellar groove is not weight-bearing.

The present study indicates that MSCs are useful in the regeneration of full-thickness articular cartilage defects.

Modifications and variations of the present invention will be obvious to those skilled in the art from the foregoing description. Such modifications are intended to come within the scope of appended claims.

We claim:

1. A composition for growing new cartilage and or bone in a patient comprising
   mesenchymal stem cells in a polymeric carrier suitable for proliferation and differentiation of the cells into cartilage and or bone.

2. The composition of claim 1 wherein the mesenchymal stem cells are isolated from muscle or dermis.

3. The composition of claim 1 wherein the polymeric carrier is biodegradable.

4. The composition of claim 1 wherein the polymeric carrier is formed of polymer fibers as a mesh or sponge.

5. The composition of claim 4 wherein the polymer is selected from the group consisting of proteins, polysaccharides, polyhydroxy acids, polyorthoesters, polyanhydrides, polymethacrylates, polyacrylates, polyphosphazenes, ethylene vinyl acetate, and polyvinyl alcohols.

6. The composition of claim 5 wherein the polymeric carrier is a polyglycolic acid fibrous mesh.

7. The composition of claim 1 wherein the polymeric carrier is a hydrogel formed by crosslinking of a polymer suspension having the cells dispersed therein.

8. The composition of claim 7 wherein the polymeric carrier is selected from the group consisting of polysaccharides and synthetic polymers.

9. A composition for growing new mixed connective tissue comprising mesenchymal cells in a polymeric carrier suitable for implantation in a fascial plane formed of muscle cells, fat, fibroblasts, and cartilage.

10. A composition for growing new articular cartilage or articular cartilage and subchondral bone in a patient comprising an effective amount of isolated mesenchymal stem cells seeded in a polymeric carrier suitable for proliferation and differentiation of the cells into articular cartilage or articular cartilage and subchondral bone.

11. The composition of claim 1 wherein the polymeric carrier is prepared from a polymer selected from the group consisting of proteins, polysaccharides, polyhydroxy acids, polyorthoesters, polyanhydrides, polyphosphazenes, and combinations thereof.

12. The composition of claim 10, wherein the polymeric carrier is prepared from a polymer selected from the group consisting of proteins, polysaccharides, polyhydroxy acids, polyorthoesters, polyanhydrides, polyphosphazenes, and combinations thereof.

13. The composition of claim 10, wherein the mesenchymal stem cells are seeded onto and into said polymeric carrier sixteen hours to two weeks prior to administration to the site.

14. The composition of claim 10 wherein the cell density of the mesenchymal stem cells is approximately 1 to 20 million cells per ml.

15. The composition of claim 1, wherein said mesenchymal stem cells comprise purified pluripotent mesenchymal stem cells, which cells are characterized by being substantially free of multinucleated myogenic lineage-committed cells, and which cells are predominantly stellate-shaped cells, wherein the mesenchymal stem cells form predominantly fibroblasic cells when contacted with muscle morphogenic protein in tissue culture medium containing 10% fetal calf serum and form predominantly branched multinucleated structures that spontaneously contract when contacted with muscle morphogenic protein and scar inhibitory factor in tissue culture with medium containing 10% fetal calf serum.

16. The composition of claim 10, wherein said isolated mesenchymal stem cells comprise purified pluripotent mesenchymal stem cells, which cells are characterized by being substantially free of mltinucleated myogenic lineage-committed cells, and which cells are predominantly stellate-shaped cells, wherein the mesenchymal stem cells form predominantly fibroblastic cells when contacted with muscle morphogenic protein in tissue culture medium containing 10% fetal calf serum and form predominantly branched multinucleated structures that spontaneously contract when contacted with muscle morphogenic protein and scar inhibitory factor in tissue culture with medium containing 10% fetal calf serum.

17. A composition for growing new articular cartilage or articular cart and subchondral bone in a patient comprising an effective amount of isolated mesenchymal stem cells seeded in a polymeric carrier suitable for proliferation and differentiation of the cells into articular cartilage or articular cartilage and subchondral bone, wherein said isolated mesenchymal stem cells are purified pluripotent mesenchymal stem cells, which cells are characterized the being substantially free of multinucleated myogenic lineage-committed cells, and which cells are predominantly stellate-shaped cells, wherein the mesenchymal stem cells form predominantly fibroblastic cells when contacted with muscle morphogenic protein in tissue couture medium containing 10% fetal calf serum and form predominantly branched multinucleated structures that spontaneously contract when contacted with muscle morphogenic protein and scar inhibitory factor in tissue culture with medium containing 10% fetal calf serum.

* * * * *